United States Patent [19]

Albright et al.

[11] Patent Number: 5,770,777
[45] Date of Patent: Jun. 23, 1998

[54] METHOD REDUCING UV ABSORPTION IN ETHYLENE GLYCOLS, WATER, AND MIXTURES

[75] Inventors: David E. Albright, Niagara Falls; Edward A. Dietz, Grand Island, both of N.Y.

[73] Assignee: Occidental Chemical Corporation, Niagara Falls, N.Y.

[21] Appl. No.: 647,289

[22] Filed: May 9, 1996

[51] Int. Cl.$^6$ .......................... C07C 45/00; C07C 27/26
[52] U.S. Cl. .......................... 568/868; 568/410
[58] Field of Search .......................... 568/868, 871, 568/852, 410

[56] References Cited

FOREIGN PATENT DOCUMENTS

| 1330350 | of 0000 | Canada . |
| 1330350 | 6/1994 | Canada . |
| R062946 | of 0000 | Romania . |

Primary Examiner—Gary Geist
Assistant Examiner—Karl J. Puttlitz, Jr.
Attorney, Agent, or Firm—Richard D. Fuerle; Arthur S. Cookfair

[57] ABSTRACT

Disclosed is a method of reducing the UV absorption of a solvent that comprises water, an ethylene glycol, or a mixture thereof, where the solvent contains at least 0.1 ppm of a dione, particularly 3-methyl-2-hydroxy cyclopent-2-eneone or its tautomer, 3-methyl-1, 2-cyclopentanedione. The solvent is passed through an anionic exchange resin containing strong base sites. The UV absorbance of the effluent from the anionic exchange resin can be monitored and, when it increases, the resin can be reactivated by passing an aqueous solution of a base through it.

20 Claims, 2 Drawing Sheets

METHOD REDUCING UV ABSORPTION IN ETHYLENE GLYCOLS, WATER, AND MIXTURES

CROSS REFERENCE TO RELATED APPLICATION

This application is related to copending application by Steven J. Qi et al., titled, "Method of Detecting Tautomeric Cyclic 1,2-Diones," Ser. No. 08/000,000, filed of even date.

BACKGROUND OF THE INVENTION

This invention relates to a method of reducing the UV absorption of a solvent which comprises an ethylene glycol, water, or a mixture thereof that contains a dione impurity. In particular, it relates to passing a solvent containing at least 0.1 ppm of a cyclic dione through an anionic exchange resin that has strong base sites.

Monoethylene glycol has many applications, including as antifreeze and as a monomer for making polyesters. Monoethylene glycol that is used to make polyesters is tested for UV absorbance, typically at 220 nm, 250 nm, and 275 nm. It is believed that high absorption at these wavelengths indicates the presence of impurities that reduce polyester quality. The absorbance at 220 nm is generally associated with the presence of organic acids, such as formic acid, and conjugated aldehydes, such as acrolein and crotonaldehyde. The compounds responsible for absorbances at 250 and 275 nm are not specifically known.

Monoethylene glycol that does not meet UV absorbance specifications must be treated or reworked before it can be used to manufacture polyesters. One method of reducing the UV absorbance is to pass the monoethylene glycol through activated carbon. While this procedure is often effective, the activated carbon must be periodically replaced or regenerated, which is a significant expenditure in capital and operating costs for a large plant.

SUMMARY OF THE INVENTION

We have discovered that cyclic diones are largely responsible for the 250 to 275 nm UV adsorption in ethylene glycols. We have further discovered that these cyclic diones can be removed from an ethylene glycol by passing it through an anionic exchange resin that contains strong base sites. Ion exchange treatment provides a cost effective alternative to activated carbon.

DESCRIPTION OF THE PREFERRED EMBODIMENTS

Figure 1:
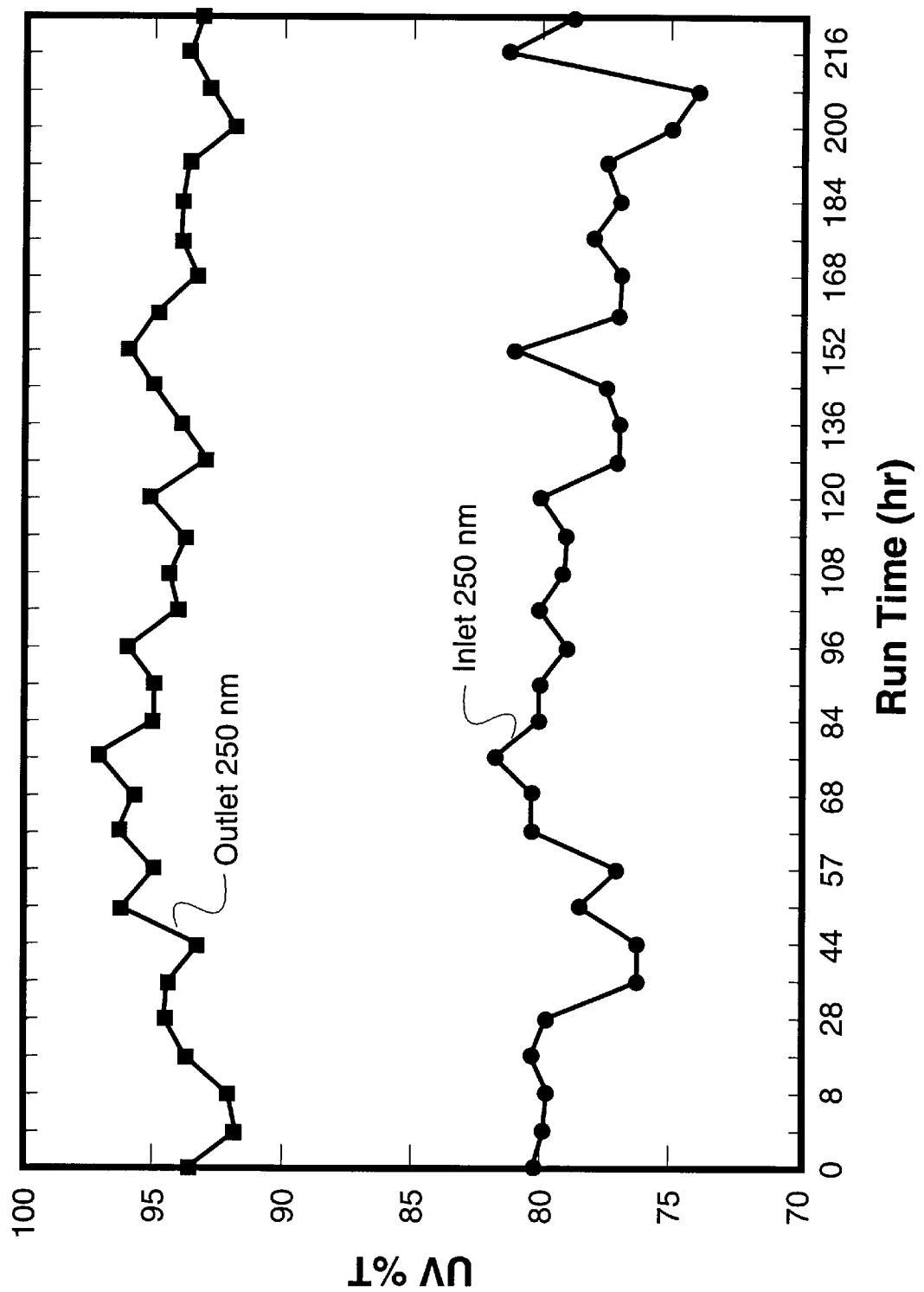
FIGS. 1 and 2 are graphs showing UV absorption at 250 and 275 nm, respectively, for a monoethylene glycol stream before and after treatment according to this invention.

This invention applies to a solvent which comprises water, an ethylene glycol (including monoethylene glycol (MEG), diethylene glycol, and triethylene glycol), or a mixture thereof with water, that contains at least 0.1 ppm of a dione, particularly a cyclic dione. If a dione is present at a concentration greater than 0.1 ppm, it can be expected to significantly increase the UV absorbance.

The invention applies to both cyclic 1,2-diones and cyclic 1,3-diones. An example of a cyclic 1,2-dione is 3-methyl-1,2-cyclopentanedione, which is tautomeric with 2-hydroxy-3-methyl-cyclopent-2-eneone (HMCP). These compounds have the formulas given below and they isomerize spontaneously so that normally both are present if one is present.

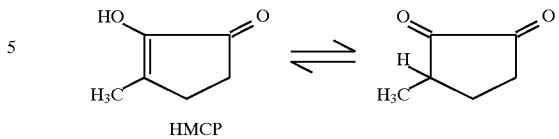

HMCP

An example of a 1,3-dione is 1,3-cyclopentanedione. The diones can be either 5-membered rings or 6-membered rings. While we do not understand the mechanism by which these cyclic diones are made during the production of ethylene glycol, we believe that they are made in some, but not all, ethylene glycol produced. The invention is also useful in treating water, an ethylene glycol, or a mixture thereof that contains a straight chain dione, where the ketone groups may or may not be vicinal.

It is not necessary to pre-treat the ethylene glycol as it is produced in some manner (other than the treatment of this invention) in order to reduce its UV absorbance. That is, it is not necessary to put other additives into the ethylene glycol or otherwise treat it prior to passing it through the anionic exchange resin in order to reduce UV absorbance. Nor is it necessary to treat the solvent with activated carbon, though that can still be done to remove other impurities.

The ethylene glycol, water, or mixture thereof is passed through an anionic exchange resin that contains strong base sites. Examples of such resins include strong base resins and weak base resins that contain at least 1% of strong base sites; typically, weak base resins contain no more than about 10% strong base sites. Strong base resins typically contain quaternary amine groups and weak base resins typically contain a tertiary amine functionality. Polystyrene or polydivinylbenzene is often used as a backbone resin. The anionic exchange resin is preferably macroporous as those resins seem to be most effective. The UV absorbance of the solvent after it passes through the resin can be monitored and, when the absorbance at 260 nm (the wavelength at which the cyclic diones absorb) increases, the resin should be considered exhausted and should be reactivated or replaced. Reactivation of the resin can be accomplished by passing an aqueous solution of a strong base through it. Alkali or alkaline earth metal hydroxides, such as 4 wt % sodium hydroxide, are preferred.

Treated ethylene glycol can be used to make polyesters. This is accomplished by reacting the ethylene glycol with a diacidic monomer such as terephthalic acid. Fibers are formed from the polyester by techniques well known in the art, such as passing a solution of the polyester through a spinerette and evaporating the solvent. Water can be treated using the process of this invention to purify it.

The following examples further illustrates this invention.

EXAMPLE 1

An ion exchange pilot bed was fabricated from a 1.8 m (6 foot) length of 5 cm (2 inch) inside diameter stainless steel pipe by attaching a bottom support plate and appropriate valves and connections. The pipe was packed about half full with a macroporous weak base resin having about 5 to 10% strong base sites, sold by Rohm & Haas as "Amberlite 96." The resin was well rinsed, backwashed, and regenerated with excess 4% caustic solution. Excess caustic was rinsed away with deionized water prior to operation.

Figure 2:
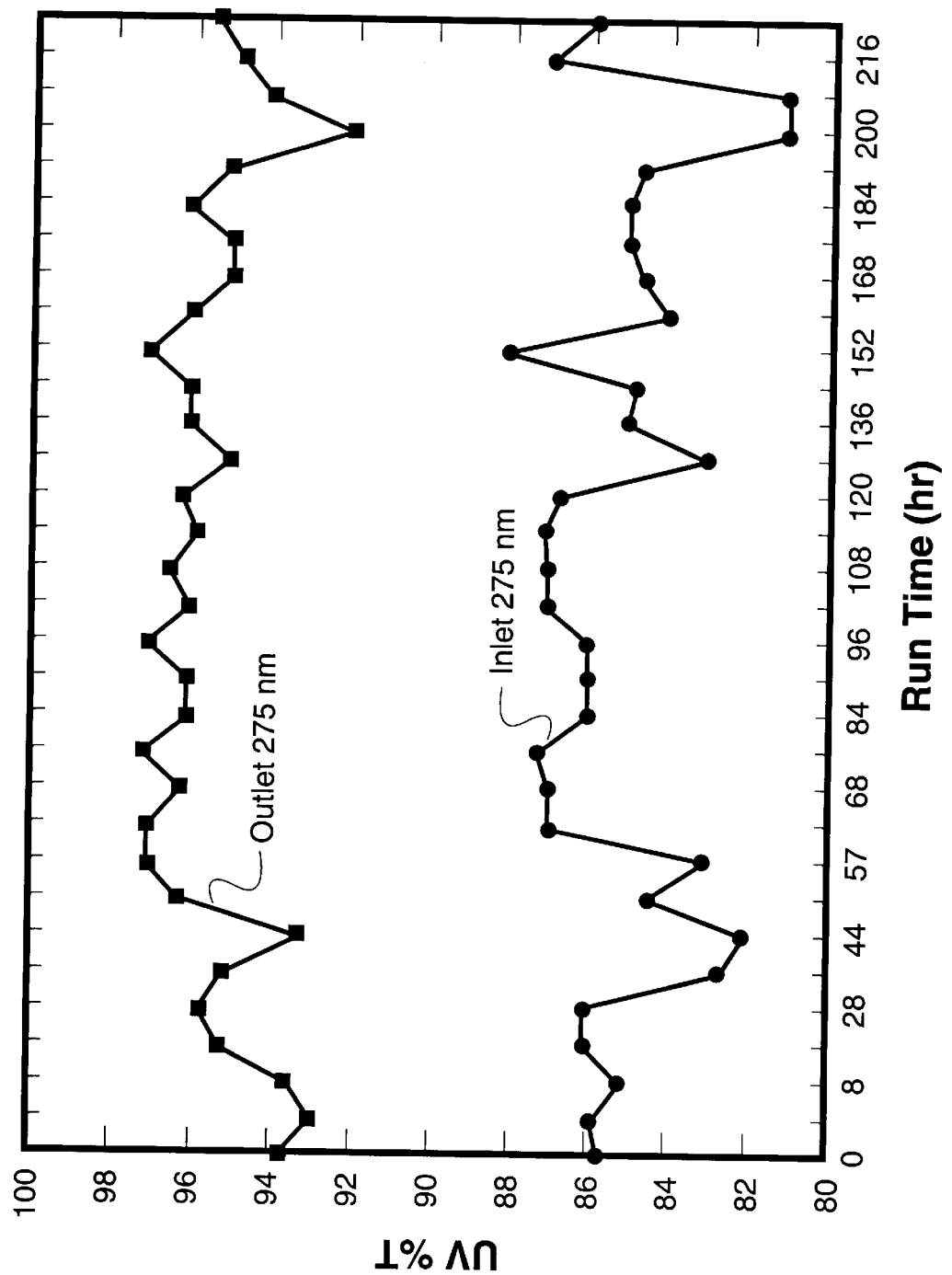

A slip stream of commercial MEG product having a low UV transmission was passed through the small column at about 15 L/minute (4 gpm). The 250 nm and 275 nm transmission (1 cm cell) of the MEG was measured at the bed inlet and outlet. In FIGS. 1 and 2, the abscissa is time and the ordinate is % transmission; inlet transmission is the lower line and outlet transmission is the higher line. FIGS. 1 and 2 show a significant improvement at 250 and 275 nm, respectively, was achieved by passing the MEG through the resin.

EXAMPLE 2

A 50 mL column was packed with 12 mL of Amerlite IRA 900 strong base ion exchange resin. To be certain the resin was pure it was regenerated with excess 4% NaOH solution and rinsed with deionized water. About 5 bed volumes of 50 ppm 1,3-cyclopentanedione (1,3-CPD) in water was passed through the resin at 2 mL/min. There was no 1,3-CPD detected in the column effluent. Next, a 1000 ppm solution of 1,3-CPD in water was passed through the column at 2 mL/min. After 5 bed volumes, there was no 1,3-CPD detected in the effluent. With a detection capability less than 0.5 ppm by UV absorbance, this result indicates that the resin effectively removed nearly all of the 1,3-CPD. Thus, the process is effective with 1,3-diones as well as 1,2-diones.

EXAMPLE 3

A 50 mL column was packed with 10 mL of Amberlite IRA 900 strong base ion exchange resin. To be certain the resin was pure it was regenerated with excess 4% NaOH solution and rinsed with deionized water. About 600 mL of a 1000 ppm HMCP aqueous solution was passed through the bed at 1 mL/minute with essentially complete HMCP removal (effluent HMCP concentration<0.1 ppm). After an additional 80 mL had been passed through the resin, the effluent concentration of HMCP had increased to the low ppm range, indicating the beginning of column breakthrough.

EXAMPLE 4

Example 3 was repeated using a 1000 ppm 2,4-pentanedione solution in water. After passing 5 bed volumes, the effluent showed no breakthrough, indicating the resin had good ability to retain this dione.

EXAMPLE 5

Example 3 was repeated using a 1000 ppm 2,3-pentadione solution in water. After passing 5 bed volumes, the effluent concentration was nearly the same as the feed indicating the resin had little ability to retain this dione.

EXAMPLE 6

A 50 mL buret was packed with 6 mL of a weak base resin based on a copolymer of polystyrene-divinylbenzene having a few percent strong base sites sold by Rohm & Haas as "Amberlite 96." The resin was washed, regenerated with excess caustic, then rinsed with DI water. MEG was passed through the resin at about 1 mL/minute. The process was continued in an attempt to establish resin capacity. After treating more than 3 L of MEG, The resin effluent still showed significant improvement over the MEG feed.

EXAMPLE 7

A 50 mL buret was packed with 6 mL of "Amberlite IRA 96" weak base resin. The resin was washed, regenerated with excess caustic, then rinsed with DI water. An aqueous solution of antifreeze grade (low quality) MEG was passed through the resin at about 1 mL/minute. No attempt was made to exhaust the resin capacity, but after 50 mL had been processed, the resin effluent showed significant improvement over the feed.

We claim:

1. A method of reducing the UV absorbance of a solvent that consists essentially of ethylene glycol, water, or a mixture thereof, and at least 0.01 ppm of a dione, comprising passing said solvent through an anionic exchange resin that contains strong base sites regenerated with hydroxide.

2. A method according to claim 1 wherein said solvent is monoethylene glycol.

3. A method according to claim 1 wherein said solvent is diethylene glycol.

4. A method according to claim 1 wherein said solvent is triethylene glycol.

5. A method according to claim 1 wherein said resin is a strong base resin.

6. A method according to claim 1 wherein said resin is a weak base resin with 1 to 10% strong base sites.

7. A method according to claim 1 wherein said dione is a cyclic dione.

8. A method according to claim 7 wherein said cyclic dione is 3-methyl-1, 2-cyclopentanedione.

9. A method according to claim 7 wherein said cyclic dione is 1,3-cyclopentanedione.

10. A method according to claim 1 wherein no additives are mixed with said solvent before it is passed through said anionic exchange resin.

11. A method according to claim 1 wherein said solvent is not passed through activated carbon.

12. A method according to claim 1 including the additional last steps of (1) monitoring the UV absorbance of the effluent from said anionic exchange resin at 260 nm; and (2) when the UV absorbance of said effluent at 260 nm increases, reactivating said anionic exchange resin by passing an aqueous solution of a base through it.

13. In a process for making an ethylene glycol that contains at least 0.01 ppm of a compound selected from the group consisting of 3-methyl-2-hydroxy cyclopent-2-eneone, its isomer, 3-methyl-1, 2-cyclopentanedione, and mixtures thereof, the improvement which comprises passing a solvent consisting essentially of said ethylene glycol and said compound through an anionic exchange resin that contains strong base sites regenerated with hydroxide, whereby said compound is removed from said ethylene glycol.

14. A method according to claim 13 wherein said ethylene glycol is unpurified and contains no additives.

15. A method according to claim 13 wherein said ethylene glycol is monoethylene glycol.

16. A method of reducing the UV absorbance of an unpurified additive-free ethylene glycol that contains at least 0.01 ppm of a compound selected from 3-methyl-2-hydroxy cyclopent-2-eneone and its isomer, 3-methyl-1, 2-cyclopentanedione comprising (A) passing said ethylene glycol through an anionic exchange resin that contains strong base sites regenerated with hydroxide;

(B) monitoring the UV absorbance of said ethylene glycol at 260 nm after it has passed through said anionic exchange resin; and (C) when said UV absorbance at 260 nm increases, re-activating said anionic exchange resin by passing an aqueous solution of a base through it.

17. A method according to claim 16 wherein said base is NaOH.

18. A method according to claim 16 wherein said ethylene glycol is monoethylene glycol.

19. A method according to claim 16 wherein said ethylene glycol is diethylene glycol.

20. A method according to claim 16 wherein said ethylene glycol is triethylene glycol.

* * * * *